United States Patent [19]

Mancini

[11] 4,039,284

[45] Aug. 2, 1977

[54] CYANURIC ACID COMPOUND COLORIMETRIC INDICATOR AND METHOD FOR USE

[75] Inventor: Thomas P. Mancini, Lincoln Park, N.J.

[73] Assignee: Coastal Industries, Inc., Carlstadt, N.J.

[21] Appl. No.: 713,991

[22] Filed: Aug. 12, 1976

[51] Int. Cl.$^2$ .................... G01N 33/18; G01N 21/20
[52] U.S. Cl. .............................. 23/230 B; 23/230 M; 252/408
[58] Field of Search ............ 23/230 R, 230 B, 230 M, 23/253 TP; 252/408

[56] References Cited
PUBLICATIONS

Morales, "Potentiometric Titrations of Cyanuric Acid and Melamine in Dimethylsulfoxide," Analytical Chem., vol. 40, No. 7, June 1968, pp. 1148–1149.

*Primary Examiner*—R.E. Serwin

[57] ABSTRACT

A formulation for colorimetric determination of the concentration of cyanuric acid compounds, particularly in swimming pool water, comprises an aqueous solution of a stabilizer, monoethanolamine and a thymolsulfonphthalein compound which, in aqueous solution with monoethanolamine, will exhibit different characteristic color shades dependent upon the concentration of cyanuric acid compounds. The stabilizer is a water-soluble, ultraviolet light absorbing material which is a condensation product of a disulfonic acid derivative with stilbene, stilbyle or their derivatives.

A method of testing for cyanuric acid compound concentrations is to mix the formulation with a sample of swimming pool water and compare the resultant characteristic color shade with a standard color shade.

17 Claims, No Drawings

CYANURIC ACID COMPOUND COLORIMETRIC INDICATOR AND METHOD FOR USE

BACKGROUND OF THE INVENTION

The present invention relates to a formulation for and a method of colorimetric testing for the concentration of cyanuric acid compounds in aqueous solution. The invention has particular application to testing for concentration of such compounds in swimming pool water and the like although the invention is not limited thereto.

As is well known, maintenance of hygienic conditions in swimming pool water and the like requires the maintaining of chlorine or a chlorine releasing compound in the water as a bactericide. It is also known that cyanuric acid compounds stabilize the chlorine or chlorine releasing compounds against excessive loss by volatilization, etc. Further, there is some ground for belief that excessive amounts of a cyanuric acid compound, or the use of certain cyanuric acid compounds, may tend to over-stabilize the chlorine releasing compound and thereby interfere with the desired bactericidal action of the chlorine. There are known and commercially available cyanuric acid compounds which, when present in the pool water within prescribed concentration limits, satisfactorily stabilize the chlorine releasing compound.

For example, potassium dichloro-s-triazinetrione (common name, potassium dichlorocyanurate) and the sodium salt of dichlorocyanurate are known stabilizing compounds. Other chlorinated cyanurics are also employed. These compounds are usually sold in powder or tablet form for use in swimming pools and the like. In aqueous solution, these compounds dissolve and dissociate so that cyanuric acid exists in equilibrium in the solution. As above indicated, it is desirable to maintain the cyanuric acid compound within a concentration range which is high enough to stablize the chlorine content against excessive losses but not so high as to possibly inhibit its bactericidal action. Experience has shown that 50 parts per million (all parts per million given herein are by weight) of the cyanuric acid compound (as cyanuric acid) is the minimum concentration for chlorine stabilization. The maximum cyanuric acid compound concentration is not more than about 200 parts per million, preferably not more than 100 parts per million (both measured as cyanuric acid). Concentrations above these levels may over-stabilize the chlorine.

It is thus apparent that for proper maintenance of swimming pool water and the like, the ability to easily and quickly determine the concentration of cyanuric acid compounds at low concentration levels (between 50 to 200 ppm) is highly desirable and the present invention is particularly applicable thereto.

Potentiometric and turbidometric methods for determination of cyanuric acid compound concentration in aqueous solution are known. However, it will be appreciated that potentiometric methods require sensitive laboratory equipment and that turbidometric methods are inherently inaccurate and difficult to read. For example, one turbidometric method uses melamine to form a precipitate of a melamine cyanuric acid salt. The quantity of preciptate formed in a sample of given size indicates the concentration of cyanuric acid compounds in the solution. But it is difficult to make an accurate estimation, particularly for an untrained operator. Such methods are too involved for the average swimming pool owner or operator to conveniently use.

Accordingly, it is an object of the present invention to provide a novel formulation which gives an easily readable colorimetric indication of the concentration of cyanuric acid compounds in aqueous solution.

It is another object of the present invention to provide such a novel formulation in the form of a single liquid which requires but dropwise addition to a sample of the aqueous solution.

It is another object of the invention to provide a novel method involving the use of such a formulation which provides a color shade characteristic of the concentration of cyanuric acid in aqueous solution, particularly at low (fifty to two hundred ppm) concentrations and one which is readily discernible to the unaided eye.

It is another object to provide a novel colorimetric test for cyanuric acid compounds which is simple enough to be used by unskilled operators.

It is yet another object of the invention to provide such a formulation which is stable both during storage, so that the formulation has a prolonged shelf life, and during exposure to bright sunlight conditions, such as those which normally prevail at swimming pools and the like.

Other objects and advantages of the invention will become apparent from the following description.

SUMMARY OF THE INVENTION

In accordance with the present invention there is provided a formulation for colorimetric determination of the concentration of cyanuric acid compounds in aqueous solution. The formulation comprises an aqueous solution of an indicator comprising a thymolsulfonphthalein compound which, when in aqueous solution with monoethanolamine, will exhibit different characteristic color shades dependent upon the concentration of cyanuric acid compounds present in solution. The thymolsulfonphthalein compound may be substituted or unsubstituted thymolsulfonphthalein salts or substituted thymolsulfonphthalein.

The formulation also includes monoethanolamine and a stabilizer. The stabilizer is a condensation product of a disulfonic acid derivative with stilbene, stilbyle or their derivatives. Its presense in the formulation, together with monoethanolamine, help to attain certain objects of the invention. The stabilizer may be a sodium salt of sulfoanilino hydroxyethyl triazin substituted stilbenes, or a sodium salt of naphthotriazole substitured stilbyles.

In accordance with another aspect of the invention, the formulation contains water in an amount to dilute the other ingredients of the formulation so that dropwise addition of the formulation to a sample of the swimming pool water or the like containing between about 20 to about 200 parts per million by weight of cyanuric acid compounds (measured as cyanuric acid) causes the different characteristic color shades to be exhibited in an intensity readily discernible to the unaided eye.

Certain objects of the invention are attained by an aspect thereof wherein the ingredients of the formulation other than water are present in the relative proportions of about 3.5 to 4.5 parts by weight of the indicator, about 9.5 to 10.5 parts by weight of monothanolamine, and about 0.4 to 0.6 parts by weight of the stabilizer.

Another aspect of the invention provides a method for colorimetric determination of the concentration of cyanuric acid compounds in aqueous solution. The method includes obtaining a sample of the solution to be tested, adding to the sample the formulation of the invention, and mixing the sample and the formulation and observing the resultant characteristic color shade. The method may further include the step of comparing the observed characteristic shade to a color shade standard which relates the characteristic color shades to specific concentrations of cyanuric acid compounds in aqueous solution.

DESCRIPTION OF THE PREFERRED EMBODIMENTS

The essential components of the formulation of the present invention are the indicator which exhibits the different characteristic color shades, monoethanolamine, and the stabilizer which prevents the other components from unduly reacting on each other while in storage and which protects the formulation against undue degradation due to exposure to ultraviolet light, i.e., sunlight. The colorimetric determination provided by the formulation of the invention means that the formulation exhibits a characteristic color shade which varies with and is dependent upon the concentration of cyanuric acid compound in the solution.

It is desired that the indicator should exhibit different color changes which are distinct enough to discriminate between different cyanuric acid compound concentrations, particularly in a very low concentration range such as between 20 to 200 parts per million or more. The color changes should be readily discernible to the unaided eye so that the unskilled operator can quickly and conveniently determine the range of cyanuric acid composition in the sample. Thymolsulfonphthalein compound indicators in aqueous solution have been found to perform this function. Particularly, sodium salts of thymolsulfonphthalein and sodium salts of thymolsulfonphthalein substituted with bromine, cresol or xylene have been found to be useful. The following specific indicator compounds have been successfully employed in the formulation of the invention: 3′, 3″ dibromo-thymolsulfonphthalein; thymolsulfonphthalein sodium salt; 3′,3″ dibromo-thymolsulfonphthalein sodium salt; 3′, 3″ dibromo-2, 5-xylenolsulfonphthalein; meta cresolsulfonphthalein.

Phenolphthalein, added as a minor component of the indicator, has been found to help promote distinctness of the color shades observed relative to various cyanuric acid compound concentrations. Generally the addition of about 10% to 20% by weight phenolphthalein (of the total weight of the mixed phenolphthalein-thymolsulfonphthalein indicator) provides satisfactory results.

The monoethanolamine not only is useful as helping to control the pH of the formulation, but it also has a surprising synergistic effect on the color change response of the formulation. This appears to be so because a number of other similar pH regulators which were tried in the formulation in place of monoethanolamine did not provide the requisite discriminatory color changes. For example, amines, other than monoethanolamine, ammonia, carbonates and hydroxide compounds all proved to be unsuccessful when an attempt was made to substitute them for monoethanolamine.

The formulation would deteriorate rather rapidly in storage and would be quickly and severely deteriorated by bright sunlight were it not for the presence of the stabilizer which serves to stabilize the other ingredients against reaction with each other and/or decomposition in storage. The stabilizer also serves to protect the formulation against ultraviolet light which would cause it to quickly react and/or decompose. The stabilizer which has been found to satisfactorily serve these functions and not interfere with the requisite discriminatory color change is a condensation product of disulfonic acid derivatives with stilbene and stilbyle and their derivatives. Specific compounds which were tested in combination with the other ingredients of the formulation and which were found to be highly satisfactorily are: 4,4′-bis[[4-anilino-6[(2-hydroxyethyl)amino]-s-triazin-2-yl]amino]-2,2′-stilbenedisulfonic acid disodium salt; 4,4′bis(4-3-sulfoanilino)-6-(bis(2-hydroxyethyl)-amino)-1,3,5-triazin-2-yl amino stilbene 2,2′ disulfonic acid, tetrasodium salt; 2-(stilbyle-4″)-(naphtho-1′, 2:4,5)-1,2,3-triazole 2″,6′-sodium disulfonic acid.

The indicator, monoethanolamine and stabilizer are prepared in aqueous solution. While the strength of the aqueous solution of the formulation could be varied to suit different needs, for the use of a colorimetric indicator for cyanuric acid compounds in swimming pool water, it is of course highly desirable that the amount of formulation required to test a small sample of swimming pool water be an amount which can be added dropwise. In other words, the solution should not be so strong that the operator must split a drop of the formulation to introduce the proper amount. On the other hand, the formulation should not be so weak that the operator must add copious amounts of formulation. Generally, it is desired that the operator be able to use a conveniently small size bottle such as an eyedropper size bottle having an eyedropper therein. The formulation strength should be such that a small test tubesize sample of water from the swimming pool or the like should require one or more eyedropper size drops therein to provide the characteristic color shade discernible to the unaided eye, for a cyanuric acid compound composition in the range of 20 to 200 parts per million or more.

This objective has been found to have been met by providing an extremely dilute aqueous solution of the formulation. As indicated by examples given below, the water content of the formulation for this purpose can be in excess of 99% by weight water.

Other than water, the proportions of the remaining ingredients required to provide discriminatory and distinct color shade changes easily discernible to the unaided eye have been found to be a major portion of monoethanolamine, a lesser portion of the indicator and a minor portion of stabilizer. Generally, relative proportions of indicator, monoethanolamine and the stabilizer are about 3.5 to 4.5 parts by weight of the indicator, about 9.5 to 10.5 parts by weight of monoethanolamine and about 0.4 to 0.6 parts by weight of the stabilizer.

More preferably, relative proportions are from about 3.68 to 4.40 parts by weight of the indicator, about 9.50 to 10.50 parts by weight of monoethanolamine and about 0.48 to 0.52 parts by weight of the stabilizer.

Formulations such as exemplified below (and many others outside the invention which were unsatisfactory) were tested as follows. Formulations were prepared and placed in shelf storage. At monthly intervals, the formulations were tested for their efficacy in providing a good color shade change responsive to the cyanuric acid solutions of known concentrations. Each formulation was tested on solutions of, respectively, 20, 50, 100, 150, and 200 ppm cyanuric acid. These concentrations were selected because they extend over the range of cyanuric acid compositions found in swimming pool water and the like. For example, 20 parts per million by weight (ppm) cyanuric acid is less than the minimum cyanuric acid content required for chlorine stabilization. Fifty ppm is the minimum required for stabilization, and it is generally agreed that the maximum acceptable cyanuric acid concentration for swimming pool water lies somewhere between 100 and 200 ppm.

Fresh cyanuric acid solutions of the above described concentrations were prepared for each monthly test. Formulations which still showed the ability to provide a satisfactory color change after one year of shelf storage were further tested against frest cyanuric acid solutions of varying alkalinity. Solutions of different alkalinity were prepared by dissolving the required amount of cyanuric acid in distilled water and adding sodium bicarbonate to prepare solutions representative of the generally accepted alkalinity range of swimming pools. For each of the above noted cyanuric acid concentrations, there was prepared a solution containing, respectivley, 50, 80, 100, and 150 parts per million by weight (ppm) sodium bicarbonate. Generally, alkalinity equivalent to 50 ppm sodium bicarbonate is too low and 150 ppm too high for swimming pool water. Eighty ppm represents generally accepted lower limit and 100 ppm represents the generally accepted upper limit. Each of these solutions was adjusted to a pH of between 7 to 8, which is the appropriate pH range for swimming pool water. Formulations in accordance with the invention provided satisfactorily discriminatory color shade changes over the entire alkalinity and cyanuric acid ranges even after one year of shelf storage.

Exemplary of the efficacy of the present invention are the following specific examples. These examples show high water dilution (99.8%+) which reflects an appropriate strength of the solution for the 20 200 ppm. concentration range of cyanuric acid concentration. Except for the quantity of water, all quantities in the examples are expressed as parts by weight.

| Example A | |
|---|---|
| thymolsulfonphthalein sodium salt | 3.7 |
| monoethanolamine | 10.0 |
| *stabilizer | 0.5 |
| Water sufficient to comprise 99.858% by weight of the formulation. | |
| Example B | |
| phenolphthalein | 0.7 |
| 3', 3- dibromo thymolsulfonphthalein sodium salt | 3.7 |
| monoethanolamine | 10.0 |
| *stabilizer | 0.5 |
| Water sufficient to comprise 99.851% by weight of the formulation. | |
| Example C | |
| 3', 3" dibromo-thymolsulfonphthalein | 3.7 |
| monoethanolamine | 10.0 |
| *stabilizer | 0.5 |
| Water sufficient to comprise 99.858% by weight of the formulation. | |
| Example D | |
| 3', 3" dibromo-thymolsulfonphthalein sodium salt | 3.7 |
| monoethanolamine | 10.0 |
| *stabilizer | 0.5 |
| Water sufficient to comprise 99.858% by weight of the formulation. | |
| Example E | |
| 3', 3" dibromo-2,5-xylenolsulfonphthalein | 3.7 |
| monoethanolamine | 10.0 |
| *stabilizer | 0.5 |
| Water sufficient to comprise 99.858% by weight of the formulation. | |
| Example F | |
| meta cresolsulfonphthalein | 3.7 |
| monoethanolamine | 10.0 |
| *stabilizer | 0.5 |
| Water sufficient to comprise 99.858% by weight of the formulation. | |

*Three efficacious versions of each of the above examples were prepared using a different one of the following as the stabilizer:
(1) 4,4'-bis[[4-anilino-6-[(2-hydroxyethyl)amino]-s-triazin-2-yl]amino]-2,2'-stilbenedisulfonic acid disodium salt;
(2) 4,4'bis(4-3-sulfoanilino)-6-(bis(2-hydroxyethyl)-amino)-1,3,5-triazin-2-yl)amino stilbene 2,2' disulfonic acid, tetrasodium salt;
(3) 2-(stilbyle-4")-(naphtho-1',2:4,5)-1,2,3-triazole 2", 6'-sodium disulfonic acid.

As indicated by the above, formulations in accordance with the present invention provide a stable composition of long shelf life capable of providing a simple colorimetric test for cyanuric acid concentration in aqueous solution, particularly useful at the low concentration levels prevalent in swimming pools and the like. The formulation permits of a method whereby a dropwise addition of the formulation to a small sized sample can provide discriminatory color changes readily discernible to the unaided eye, thereby facilitating testing of swimming pools by operators unskilled in laboratory techniques, and without need for equipment or the like. A sample of the pool water is obtained and the formulation added thereto. Only a drop or two of the formulation is required for a small test tube size sample. The sample and formulation are mixed or shaken and a blue-green color will develop depending on the concentration of cyanuric acid compounds present. A standard color chart with the colors keyed to the associated concentration of cyanuric acid compound may be provided and the color of the sample compared to the color chart to estimate the cyanuric acid compound concentration.

Obviously, the formulation and the method of the invention are not limited to testing for cyanuric acid compounds in swimming pool water, but are of general applicability as a colorimetric test for cyanuric acid concentration in any aqueous solution. Different strengths for the formulation may be appropriate for different concentration ranges to permit color shade observation with the unaided eye or with optical devices as desired.

Having thus described the invention, I claim:

1. A formulation for colorimetric determination of the concentration of cyanuric acid compounds in aqueous solution comprising an aqueous solution of:
   a. an indicator comprising a thymolsulfonphthalein compound which, in aqueous solution with monoethanolamine, exhibits different characteristic color shades dependent upon the concentration of cyanuric acid compounds present in solution;
   b. monoethanolamine; and
   c. a stabilizer which is a condensation product of a disulfonic acid derivative with a compound selected from the class consisting of stilbene, stilbyle and their derivatives.

2. The formulations of claim 1 wherein said indicator further includes phenolphthalein.

3. The formulation of claim 1 wherein said thymolsulfonphthalein compound is selected from the class consisting of substituted and unsubstituted thymolsulfonphthalein salts and substituted thymolsulfonphthaleins, and said stabilizer is selected from the class consisting of sodium salts of sulfonilino-hydroxyethyl triazin-substituted stilbenes and sodium salts of naphthotriazole substituted stilbyles.

4. The formulation of claim 3 wherein said thymolsulfonphthalein salts are sodium salts and said substituted thymolsulfonphthaleins have substituents selected from the class consisting of bromine, cresol and xylene.

5. The formulation of claim 1 wherein the color change indicator is selected from the class consisting of thymolsulfonphthalein sodium salt; 3',3" dibromo-thymolsulfonphthalein sodium salt plus phenolphthalein; 3',3" dibromo thymolsulfonphthalein; 3',3" dibromo-thymolsulfonphthalein sodium salt 3', 3" dibromo-2, 5-xylenolsulfonphthalein; and meta-cresolsulfonphthalein; and the stabilizer is selected from the class consisting of 4,4'-bis [[4-anilino-6[(2-hydroxyethyl) amino]-s-triazin-2-yl]amino[-2,2'-stilbenedisulfonic acid disodium salt; 4,4'bis (4-3-sulfoanilino)-6-(bis(2-hydroxyethyl)-amino)-1,3,5-triazin-2,yl amino stilbene 2,2' disulfonic acid, tetrasodium salt; and 2-(stilbyle-4")-(naphtho-1',2:4, 5)-1,2,3-triazole 2",6'-sodium disulfonic acid.

6. The formulation of claim 1 wherein the ingredients other than water are present in the proportions of about 3.5 to 4.5 parts by weight of said indicator, about 9.5 to 10.5 parts by weight of monoethanolamine and about 0.4 to 0.6 parts by weight of said stabilizer.

7. The formulation of claim 6 wherein said indicator comprises a minor portion of phenolphthalein and a major portion of said thymolsulfonphthalein compound.

8. The formulation of claim 6 wherein water comprises at least about 99% by weight of the formulation.

9. A formulation for colorimetric detection of cyanuric acid compounds in swimming pool water and the like comprising an aqueous solution of:
  a. an indicator which, in aqueous solution with monoethanolamine, exhibits different characteristic color shades dependent upon the concentration of cyanuric acid compounds in the solution and selected from the class consisting of substituted and unsubstituted thymolsulfonphthalein salts and substituted thymolsulfonphthaleins;
  b. monoethanolamine; and
  c. a stabilizer which is a water soluble, ultraviolet light absorbent condensation product of a disulfonic acid derivative with a compound selected from the class consisting of stilbene and its derivatives.

10. The formulation of claim 9 wherein said indicator is selected from the class consisting of thymolsulfonphthalein sodium salt; 3',3" dibromo-thymolsulfonphthalein sodium salt plus phenolphthalein; 3',3" dibromo-thymolsulfonphthalein; 3',3" dibromo-thymolsulfonphthalein sodium salt; 3',3" dibromo-2, 5-xylenolsulfonphthalein; and meta-cresolsulfonphthalein; and wherein the stabilizer is selected from the class consisting of 4,4'-bis[[4-anilino-6[(2-hydroxyethyl)amino]-s-triazin-2-yl]amino]-2,2'-stilbenedisulfonic acid disodium salt; 4,4' bis(4-3-sulfoanilino)-6-(bis(2-hydroxyethyl)-amino)-1,3,5-triazin-2-yl amino stilbene 2,2' disulfonic acid, tetrasodium salt; and 2-stilbyle-4")-naphtho-1',2:4,5)-1,2,3-triazole 2",6'-sodium disulfonic acid.

11. The formulation of claim 9 containing water in an amount to dilute the other ingredients of the formulation so that dropwise addition of the formulation to a sample containing between about 20 to about 200 parts per million by weight cyanuric acid compounds causes the different characteristic color shades to be exhibited in an intensity discernible to the unaided eye, and wherein the other ingredients are present in the following relative proportions: said indicator from about 3.5 to 4.5 parts by weight; said monoethanolamine from about 9.5 to 10.5 parts by weight; and said stabilizer from about 0.4 to 0.6 parts by weight.

12. The formulation of claim 11 wherein said indicator comprises a minor portion of phenolphthalein and a major portion of the thymolsulfonphthalein compound.

13. The formulation of claim 12 wherein said other ingredients are present in the following relative proportions: said indicator from about 3.68 to 4.40 parts by weight; said monoethanolamine from about 9.50 to 10.50 parts by weight; and said stabilizer from about 0.48 to 0.52 parts by weight.

14. The formulation of claim 10 in which said indicator is thymolsulfonphthalein sodium salt and the ingredients other than water are present in the following approximate relative proportions: said indicator about 3.7 parts by weight; said monoethanolamine about 10.0 parts by weight; and said stabilizer about 0.5 parts by weight.

15. The formulation of claim 10 in which said indicator is phenolphthalein plus 3',3" dibromo-thymolsulfonphthalein sodium salt and the ingredients other than water are present in the following approximate relative proportions: said indicator about 4.4 parts by weight; said monoethanolamine about 10.0 parts by weight; and said stabilizer about 0.5 parts by weight.

16. A method for colorimetric determination of the concentration of cyanuric acid compounds in aqueous solution comprising the steps of:
  a. obtaining a sample of said solution;
  b. adding to said sample a formulation comprising an aqueous solution of:
    1. a thymolsulfonphthalein compound which, in aqueous solution with monoethanolamine, exhibits characteristic color shades which are dependent upon the concentration of cyanuric acid compound in said aqueous solution;
    2. monoethanolamine; and
    3. a stabilizer which is a condensation product of disulfonic acid derivatives with a compound selected from the class consisting of stilbene, stilbyle and their derivatives; and
  c. mixing said sample and said formulation and observing the resultant characteristic color shade of the mixed sample and formulation.

17. The method of claim 16 further including the step of comparing the observed characteristic color shade to a color shade standard which relates the characteristic color shades to concentrations of cyanuric acid compounds in aqueous solution.

* * * * *

UNITED STATES PATENT AND TRADEMARK OFFICE
CERTIFICATE OF CORRECTION

PATENT NO. : 4,039,284
DATED : August 2, 1977
INVENTOR(S) : Thomas Mancini

It is certified that error appears in the above-identified patent and that said Letters Patent are hereby corrected as shown below:

Column 4, line 11, after "yl" insert --)--;

Column 6, line 47, "formulations" should be -- formulation --;

Column 7, line 1, "[" should be -- ] --;

Column 7, line 3, "2,yl" should be -- 2-yl)--;

Column 7, line 44, after "yl" insert -- ) --;

Column 7, line 45 "2-stilbyle-4")-naphtho-1',2:4,5)-" should be -- 2-(stilbyle-4")-(naphtho-1',2:4,5)- --.

Signed and Sealed this

Fourteenth Day of March 1978

[SEAL]

Attest:

RUTH C. MASON
Attesting Officer

LUTRELLE F. PARKER
Acting Commissioner of Patents and Trademarks